(12) United States Patent
Carmody

(10) Patent No.: US 6,468,512 B1
(45) Date of Patent: Oct. 22, 2002

(54) GEL COMPOSITIONS

(75) Inventor: Walter J. Carmody, Port Jervis, NY (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 09/718,874

(22) Filed: Nov. 22, 2000

(51) Int. Cl.[7] .............................. A61K 7/32; A61K 7/34; A61K 7/36; A61K 7/38; A61K 7/00

(52) U.S. Cl. ............................. 424/65; 424/66; 424/67; 424/68; 424/400; 424/406

(58) Field of Search ................. 424/65, 66, 67, 424/68, 400, 401

(56) References Cited

U.S. PATENT DOCUMENTS

| | | | |
|---|---|---|---|
| 4,263,274 A | 4/1981 | Kulkarni et al. | 424/46 |
| 4,605,554 A | 8/1986 | Prussin et al. | 424/66 |
| 4,673,570 A | 6/1987 | Soldati | 424/66 |
| 4,782,095 A | 11/1988 | Gum | 514/937 |
| 4,944,938 A | 7/1990 | Potini | 424/68 |
| 4,948,938 A | 8/1990 | Vignes | 219/121.14 |
| 5,162,378 A | 11/1992 | Guthauser | 514/785 |
| 5,393,518 A | 2/1995 | Kwass | 424/66 |
| 5,499,511 A | 3/1996 | Hara et al. | 62/180 |
| 5,508,024 A | 4/1996 | Tranner | 424/59 |
| 5,520,907 A | 5/1996 | Orofino et al. | 424/65 |
| 5,587,153 A | 12/1996 | Angelone, Jr. et al. | 424/66 |
| 5,925,338 A | 7/1999 | Karassik et al. | 424/65 |
| 6,063,365 A | 5/2000 | Shefer et al. | 424/65 |

*Primary Examiner*—Shelley A. Dodson
(74) *Attorney, Agent, or Firm*—Ohlandt, Greeley, Ruggiero & Perle, LLP

(57) ABSTRACT

There is provided a clear antiperspirant/deodorant gel composition. The composition is a water-in-oil emulsion having a viscosity about 7,000 cps to about 25,000 cps and a clarity from about 30 NTU or less. The composition further has an antiperspirant active, water, silicone gelling agent, and one or more silicone oils.

53 Claims, No Drawings

GEL COMPOSITIONS

BACKGROUND OF THE INVENTION

1. Field of the Invention

The present invention relates to a clear antiperspirant and/or deodorant gel composition for application to the skin. More particularly, the present invention relates to a gel composition that exhibits a soft feel to the skin when applied. Still more particularly, the present invention relates to a gel composition that provides a high degree of antiperspirant efficacy. It is believed that this gel composition has improved aesthetics and performance due, among other things, to its viscosity that is between about 7,000 centipoise (cps) to about 25,000 cps at 25 degrees C.

2. Description of the Prior Art

Antiperspirant/deodorant compositions are commonly applied to the skin at the underarms to prevent or alleviate sweating and/or odor. Such compositions take a variety of physical forms such as a stick, gel, cream, roll-on liquid, pump spray and aerosol spray.

A popular form of an antiperspirant/deodorant composition is the gel. Gels can be made transparent (clear), translucent, or opaque. Clear gel compositions are particularly aesthetically pleasing to consumers. Conventional clear gel compositions typically take the form of water-in-silicone emulsions with an antiperspirant active.

A problem commonly encountered with antiperspirant/deodorant gel compositions is stiffness. When a gel composition is stiff, it does not spread easily on the skin. When applied by a user, coverage on the skin may be non-uniform. Non-uniformity of coverage reduces the evaporation rate of volatiles, which can cause a tacky or sticky feel on the skin. Also, the gel composition may be slow to dry.

The prior art sets forth 3 variety of antiperspirant/deodorant compositions. They include those disclosed in U.S. Pat. Nos. 4,122,029; 4,268,499; 4,363,988; 4,673,570; 4,719,103; 4,725,431; 4,782,095; 4,944,938; 4,948,938; 5,162,378; 5,393,518; 5,449,511; 5,492,691; 5,520,907; 5,587,153; 5,925,338; 5,939,055 and 6,063,365.

U.S. Pat. No. 4,673,570 relates to clear gel compositions having a silicone emulsifier with a viscosity of 600 centipoise (cps) to 2,000 cps. U.S. Pat. No. 5,393,518 provides an antiperspirant composition having cyclomethicone, aluminum zirconium tetrahydrochoride and dimethicone copolyol, with a viscosity less than 1,000 cps. U.S. Pat. No. 5,587,153 relates to clear gel compositions in the form of a water in silicone emulsion. The composition has a viscosity of 50,000 cps to 200,000 cps, a clarity of 50 nephelomedric turbidity units (NTU) or less, and a refractive index of 1.3975 to 1.4025. U.S. Pat. No. 5,925,338 relates to gel compositions in the form of water-in-silicone emulsions of a viscosity of 50,000 cps to 250,000 cps.

U.S. Pat. No. 5,449,511 is directed to anhydrous, solid antiperspirant compositions having 48.1% cyclomethicone, 22.7% aluminum zirconium tetrahydrochoride and 5% dimethicone copolyol.

U.S. Pat. No. 6,063,365 provides a gel composition having aluminum chlorohydrate, dimethicone, cyclomethicone, dimethicone copolyol, and water.

The gel compositions of the prior art are too stiff to effectively apply uniformly to the skin to enhance antiperspirant/deodorant efficacy. It would be desirable to have a gel composition that could be applied uniformly.

It would further be desirable to have a gel composition that provided enhanced antiperspirant activity. The prior art has discussed the use of formaldehyde as an antiperspirant active. U.S. Pat. No. 4,263,274 provides that formaldehyde has anhydrotic properties but is not useful due to strong odor, irritating effects on the skin and/or high skin permeability or skin staining. U.S. Pat. No. 5,508,024 provides that aldehydes, such as formaldehyde, can suppress sweating but that their sensitization potential has prevented commercialization. *Antiperspirants and Deodorants*, Marcel Dekker, p.108–109, (1988) points out that formaldehyde is an effective antiperspirant but that it has not been commercialized due to its sensitizing capability. U.S. Pat. No. 4,605,554 provides roll-on liquid or powder antiperspirant/deodorant compositions. Formaldehyde donors are disclosed as deodorant chemicals. No antiperspirant activity is disclosed.

It would be desirable to have an antiperspirant/deodorant gel composition that delivers formaldehyde as an antiperspirant active. It would be desirable to have such a gel composition that delivers formaldehyde without undue skin sensitization.

SUMMARY OF THE INVENTION

It is an object of the present invention to provide a gel composition that affords excellent antiperspirant and/or deodorant protection from bodily sweating and/or odor.

It is another object of the present invention to provide such a gel composition that is substantially clear and aesthetically appealing.

It is a further object of the present invention to provide such a gel composition that is soft to the touch yet provides excellent coverage and physical integrity at the surface of the skin, particularly the underarms.

It is still a further object of the present invention to provide a method of decreasing perspiration from human skin comprising applying to the skin the clear antiperspirant/deodorant gel composition described above.

These and further objects and advantages of the present invention are achieved by a clear antiperspirant/deodorant gel composition that takes the form of a water-in-oil emulsion having a viscosity of about 7,000 cps to about 25,000 cps.

The gel composition may also include a formaldehyde donor as an antiperspirant active or as an antiperspirant enhancer, and may deliver such formaldehyde donor in a manner that the skin is substantially not sensitized or irritated.

DETAIL DESCRIPTION OF THE INVENTION

It was surprising that an antiperspirant/deodorant gel composition could be formulated that could be easily and uniformly spread on the skin, yet dry quickly. It was also surprising that such gel composition could be formulated to feel soft and provide excellent antiperspirant activity. It was still further surprising that such gel composition could be formulated to appear clear and aesthetically pleasing.

The gel composition of the present invention takes the form of a water-in-oil emulsion, preferably a water-in-silicone emulsion. The composition has a viscosity from about 7,000 centipoise (cps) to about 25,000 cps. Also, the composition preferably exhibits a clarity from about 30 NTU or less. The gel composition further has about 5 percentage by weight (wt. %) to about 50 wt. % of an antiperspirant active, about 25 wt. % to about 45 wt. % water, about 0.1 wt. % or more of a silicone gelling agent, and about 9.0 wt. % or more of one or more silicone oils, based upon the total weight of the composition.

An important aspect of the present invention is the viscosity of the gel composition. Viscosity of the gel composition is important in imparting desired physical properties and feel to the skin. If viscosity is too high, the gel composition is too stiff and may be difficult to spread uniformly on the skin. Non-uniform application decreases efficacy and increases the amount of time required for volatiles to evaporate. Slow evaporation results in longer drying time. In general, high viscosity can result in the gel composition feeling wet and sticky to the consumer for an unacceptably long period of time. If viscosity is too low, the gel composition will feel wet and sticky to the user for an even unacceptably longer period of time, probably due to a very high oil content.

In the present invention, it has been discovered that a gel composition having a viscosity range from about 7,000 cps to about 30,000 cps, preferably to about 25,000 cps, more preferably from about 12,000 cps to about 21,000 cps, and most preferably from about 18,000 cps to about 21,000 cps, provides significantly improved physical properties and characteristics. Such viscosity is low enough to facilitate excellent spreading and uniform coverage on the skin, yet is high enough to avoid an excessive oil content.

The present gel composition has an antiperspirant active to reduce body sweating and, consequently, odor. Preferably, the antiperspirant active is present in the gel composition from about 5 wt. % to about 50 wt. %, based on the total weight of the composition. More preferably, the antiperspirant active is present from about 15 wt. % to about 25 wt. %, based on the total weight of the composition. Antiperspirant actives that can be used in the present composition include, but are not limited to, aluminum chlorohydrate; aluminum zirconium trichlorohydrate, tetrachlorohydrate, pentachlorohydrate, and octachlorohydrate; aluminum zirconium trichlorohydrex-gly, tetrachloroydrex-gly, and pentachlorohydrex-gly, and octachlorohydrex-gly; and calcium chloride and other metal halide salts capable of reducing body sweating.

The present invention preferably includes in the gel composition a substantial amount of water. The amount of water may range from about 25 wt. % to about 45 wt. % of the total weight of the composition. The relatively high water content enables the proportion of glycols and silicone oils in the gel composition to be reduced. In addition to saving on ingredient cost, namely less of the more expensive glycol versus water, the reduced glycol content facilitates the evaporation of the volatile silicone and the water.

It was very surprising to find that the composition of the present invention was able to comprise a relatively high amount of water, yet have excellent physical integrity of the gel, feel soft to the touch, be substantially transparent, apply uniformly, and have improved antiperspirant efficacy.

The present gel composition also has a silicone emulsifier that acts as a gelling agent and one or more volatile and/or non-volatile silicone oils. Silicone gelling agents provide a gel matrix and bulk for the gel composition. The gelling agents act as emulsifiers in forming the water into silicone emulsions or gels. The silicone oils function to thicken and soften the gel composition and provide softening and conditioning effects to the skin.

The silicone gelling agent is present in the gel composition at about 0.1 wt. % or more, and preferably about 0.5 wt. % to about 5.0 wt. %, based on the total weight of the composition. More preferably, the silicone gelling agent is about 0.5 wt. % to about 1.5 wt. %, based on the total weight of the composition.

Silicone gelling agents that can be used in the composition of the present invention include, but are not limited to, dimethicone copolyol (polyether substituted dimethicone), laurylmethicone copolyol, cetyl dimethicone copolyol and stearyl dimethicone copolyol. Dimethicone copolyol is described in U.S. Pat. No. 4,122,029, which is incorporated herein by reference. The preferred silicone gelling agent, dimethicone copolyol, is a mixture of 10% dimethicone copolyol and 90% cyclomethicone. The former acts as a gelling agent, while the latter acts as a solvent.

The silicone oils used in the present composition typically have boiling points below about 250° C.

Such silicone oils include volatile silicone oils, such as cyclomethicone (pentamer is preferred; tetramer; hexamer; and mixtures thereof) and dimethicone having a viscosity of about 0.65 to about 2 centistokes. Non-volatile silicone oils that can be used in the present composition include high molecular weight polysiloxanes, high viscosity linear dimethicones, namely from about 5 to about 100,000 ceritistokes, phenyl trimethicone cetyl dimethicone and stearyl dimethicone. The preferred range for the silicone oil is from about 9 wt % to about 30 wt %, based on the total weight of the composition.

A preferred combination of a volatile silicone oil and a silicone gelling agent is a cyclometriicone/dimethicone copolyol blend. This blend is sold commercially as DC 5225C and DC 3225C by Dow Corning Corporation as a 90/10 by weight blend. The blend is also commercially available under the trade names SF 1528 from General Electric Silicones.

The gel composition may have non-silicone co-gelling agents or thickeners, if desired. Such co-gelling agents include: cellulose derivatives, such as carboxymethylcellulose, methylcellulose, hydroxypropylmethylcellulose and hydroxyethylcellulose; carrageenan gum; xanthan gum; tragacanth gum; caraya gum; gum arabic; polysodium acrylate; and, polyvinyl pyrrolidone. A preferred co-gelling agent is a cationic hydroxyethyl cellulose. The preferred cationic hydroxyethyl cellulose is Polyquaternium-10, and is sold by National Starch. The co-gelling agent may be used together with or in place of the silicone gelling agent.

The emulsion of the present gel composition can be formulated with any emulsifier or surfactant known in the art as useful in water-in-oil emulsions. Such emulsifiers and surfactants that can be used in the present invention include, but are not limited to, Steareth-2, Steareth-20, PPG 5-Ceteth-20 and POE (20M) Sorbitan Monolaurate. Additional useful emulsifiers, co-emulsifiers, and surfactants are provided in U.S. Pat. No. 5,162,378 (column 4), which is incorporated herein by reference.

The present gel composition may be formulated to exhibit a high degree of clarity by means known to those skilled in the art. Clarity can be characterized on the basis of turbidity and/or index of refraction.

The present gel composition preferably exhibits clarity from about 5 nephelomedric turbidity units (NTU) to about 30 NTU, and more preferably about 10 NTU to about 20 NTU. The present gel composition also preferably exhibits an index of refraction from about 1.39 to about 1.41, and preferably 1.399 to 1.405. Refractive index modifiers can be added to either or both of the oil or water phases to modify index of refraction. Preferably, the oil and water phases of the gel composition exhibit indices of refraction within 0.0004 of each other to provide a preferred level of overall clarity to the composition.

Representative refractive index modifiers together with their respective indices of refraction are listed in the Table below. The listing also includes colorants, which may be added to gel compositions to modify refractive index, mask off colors of antiperspirant actives or other ingredients, or provide a desired product color for aesthetic appeal. The listing is representative and not to be construed as limiting.

TABLE

Refractive Index Modifiers

| Water soluble | |
|---|---|
| Propylene glycol | 1.4300 |
| Dipropylene glycol | 1.4377 |
| Butylene glycol | 1.4400 |
| Glycerin | 1.4675 |
| Sorbitol, 70% aq. | 1.4600 |
| Water | 1.3340 |
| FD&C Red #33 (2% solution) | 1.3591 |
| FD&C Blue #1 (2% solution) | 1.3582 |
| FD&C Yellow #10 (2% solution) | 1.358 |
| Oil soluble | |
| Dimethicone | 1.4030 |
| Mineral Oil | 1.4590 |
| Isopropyl Palmitate | 1.4367 |
| Diisopropyl Adipate | 1.4230 |
| Phenyl Trimethicone | 1.4600 |
| Ethanol | 1.3630 |

Both turbidity and refractive index impact the overall clarity of the present composition, but do not account for the improved aesthetic feel of the composition on one's skin.

In a preferred embodiment, the gel composition has a formaldehyde donor therein. The formaldehyde donor functions both as a preservative and as an antiperspirant in the gel composition. Formaldehyde donors are known in the cosmetic and personal care product art as being useful in preservative or antimicrobial applications. However, heretofore they have not been appreciated as commercially practical antiperspirant actives. In the present invention, it was unexpectedly found that formaldehyde donors exhibited significant antiperspirant activity in a gel composition. The gradual release of formaldehyde by the donors permits bodily sweating to be reduced while substantially avoiding the skin sensitization problems normally encountered when significant amounts of formaldehyde are directly utilized in the composition.

Formaldehyde donors useful in the present invention include, but are not limited to, diazolidinyl urea, DMDM hydantoin, imidazolidinyl urea, Quaternium-15 (Dowicil 200) and a combination thereof. Formaldehyde donors can also serve as enhancers for conventional antiperspirant actives such as those described above in the present gel composition, or other product forms such as sticks, creams, emulsions, sprays and roll-ons.

It is understood that the present gel composition may optionally contain other ingredients, such as one or more analgesics, antibacterials, antlmicrobials, anti-allergenics, chelating agents, colorants, fragrances, lubricants, moisturizers, preservatives, skin protectants, stabilizers, sunscreens, surfactants, vitamins, and the like.

EXAMPLES

Antiperspirant/deodorant gel compositions of the present invention were prepared and tested for physical properties.

Gel compositions were generally prepared by forming separate oil and water phases (referred to in the Examples as phases A and B, respectively). The refractive indices of the phases were measured, and the refractive index of the aqueous phase was adjusted, if necessary. The refractive index of the aqueous phase was adjusted by adding water in small amounts to lower it, or by adding dipropylene glycol, propylene glycol or other water soluble refractive index modifiers in small amounts to increase it. Refractive indices of each phase were adjusted to within 0.0004 units of each other to enhance the clarity achieved in the overall emulsion.

After refractive indices were adjusted, phase A was stirred moderately, then added to phase B. The phase mixture was blended until uniform. Then, the phase mixture was blended in a high shear mixer until the desired viscosity was attained. The resulting gel compositions were packed in airtight containers for storage until physical properties testing.

The gel compositions were tested for refractive index, pH, viscosity, and turbidity. All tests were conducted at 77° F. unless otherwise noted. All compositions were tested as neet material. Neet means full strength and as is. In other words, it is without the addition of an optional ingredient(s). Refractive index was measured using Bausch and Lomb Abbe Refractometer. The "pH" was measured with a Beckman Model 40 pH meter and a Orion 81-72BN probe. However, during the pH test, dilution is required so that, for this test, the compositions are no longer neet. Viscosity was measured with a Brookfield model RVF viscometer with spindle #4 or #5 at 20 rpm for one minute. Clarity was measured with a Hach model 18900 Ratio Turbidimeter.

Aluminum chlorohydrate, as a 50% solution in the Examples, means 50% aluminum chlorohydrate and 50% water. Cyclomethicone/dimethicone copolyol in the Examples is a blend of 90% cyclomethicone and 10% dimethicone copolyol. All percentages are by weight unless otherwise indicated.

Example 1

| Phase A | | |
|---|---|---|
| Cyclomethicone, pentamer | | 8.00% |
| Cyclomethicone/Dimethicone Copolyol | | 9.00% |
| Phase B | | |
| Aluminum Chlorohydrate, 50% solution | | 50.00% |
| Dipropylene Glycol | | 14.70% |
| Demineralized Water | | 18.00% |
| Imidazolinyl Urea | | 0.20% |
| PPG 5-Ceteth-20 | | 0.10% |
| Refractive index: | Phase A | 1.4000 |
| | Phase B | 1.4000 |
| | Gel | 1.4000 |
| pH | | 3.82 |
| Viscosity | | 21,000 cps |
| Clarity | | 15 NTU |

Example 2

| Phase A | |
|---|---|
| Cyclomethicone, pentamer | 7.50% |
| Isopropyl Myristate | 0.20% |
| Cyclomethicone/Dimethicone Copolyol | 9.00% |
| Ethanol | 1.00% |
| Fragrance | 0.20% |

-continued

| Phase B | | |
|---|---|---|
| Aluminum Chlorohydrate | | 50.00% |
| Dipropylene Glycol | | 14.00% |
| Demineralized Water | | 17.70% |
| Imidazolinyl Urea | | 0.30% |
| PPG 5-Ceteth-20 | | 0.10% |
| Refractive index: | Phase A | 1.3987 |
| | Phase B | 1.3986 |
| | Gel | 1.3986 |
| pH | | 3.79 |
| Viscosity | | 18,500 cps |
| Clarity | | 14 NTU |

Example 3

| Phase A | | |
|---|---|---|
| Cyclomethicone, pentamer | | 7.50% |
| Isopropyl Myristate | | 0.10% |
| Cyclomethicone/Dimethicone Copolyol | | 8.80% |
| Fragrance | | 0.20% |
| Phase B | | |
| Aluminum Chlorohydrate, 50% solution | | 50.00% |
| Dipropylene Glycol | | 14.20% |
| Demineralized Water | | 18.50% |
| Diazolidinyl Urea | | 0.40% |
| POE (20 M) Sorbitan Monolaurate | | 0.30% |
| Refractive index: | Phase A | 1.3992 |
| | Phase B | 1.3994 |
| | Gel | 1.3993 |
| pH | | 3.83 |
| Viscosity | | 19,000 cps |
| Clarity | | 18 NTU |

Example 4

| Phase A | | |
|---|---|---|
| Cyclomethicone, tetramer | | 14.50% |
| Isopropyl Palmitate | | 7.00% |
| Dimethicone | | 3.00% |
| Cyclomethicone/Dimethicone Copolyol | | 7.00% |
| Fragrance | | 0.10% |
| Phase B | | |
| Aluminum Chlorohydrate, 50% Solution | | 50.00% |
| Dipropylene Glycol | | 12.50% |
| Demineralized Water | | 5.60% |
| POE (20 M) Sorbitan Monolaurate | | 0.30% |
| Refractive index: | Phase A | 1.4105 |
| | Phase B | 1.4107 |
| | Gel | 1.4106 |
| pH | | 3.82 |
| Viscosity | | 12,000 cps |
| Clarity | | 16.8 NTU |

Example 5

| Phase A | | |
|---|---|---|
| Cyclomethicone, pentamer | | 16.00% |
| Isopropyl Palmitate | | 7.00% |
| Dimethicone | | 2.00% |

-continued

| | | |
|---|---|---|
| Cyclomethicone/Dimethicone Copolyol | | 6.00% |
| Fragrance | | 0.50% |
| Phase B | | |
| Al/Zr Tetra Chlorohydrex-gly, 45% sol. | | 49.90% |
| Diproplyene Glycol | | 12.00% |
| Demineralized Water | | 6.20% |
| POE (20 M) Sorbitan Monolaurate | | 0.40% |
| Refractive index: | Phase A | 1.4131 |
| | Phase B | 1.4134 |
| | Gel | 1.4133 |
| pH | | 3.70 |
| Viscosity | | 7500 cps |
| Clarity | | 25 NTU |

Example 6

| Phase A | | |
|---|---|---|
| Cyclomethicone, pentamer | | 7.00% |
| Cyclomethicone/Dimethicone Copolyol | | 10.00% |
| Phase B | | |
| Aluminum Chlorohydrate, 50% Solution | | 50.00% |
| Propylene Glycol | | 16.00% |
| Demineralized Water | | 17.00% |
| Refractive index: | Phase A | 1.3995 |
| | Phase B | 1.3974 |
| | Gel | 1.3974 |
| pH | | 3.91 |
| Viscosity | | 21,000 cps |
| Clarity | | 20 NTU |

Example 7

| Phase A | | |
|---|---|---|
| Cyclomethicone, pentamer | | 7.00% |
| Dimethicone, 50 centistokes | | 3.00% |
| Cyclomethicone/Dimethicone Copolyol | | 7.00% |
| Fragrance | | 0.10% |
| Phase B | | |
| Aluminum Chlorohydrate, 50% Solution | | 50.00% |
| Dipropylene Glycol | | 14.90% |
| Demineralized Water | | 17.70% |
| Imidazolinyl Urea | | 0.20% |
| POE (20 M) Sorbitan Monolaurate | | 0.10% |
| Refractive index: | Phase A | 1.4000 |
| | Phase B | 1.3996 |
| | Gel | 1.3999 |
| pH | | 3.81 |
| Viscosity | | 19,500 cps |
| Clarity | | 18 NTU |

Example 8

| Phase A | |
|---|---|
| Cyclomethicone, pentamer | 19.00% |
| Cyclomethicone/Dimethicone Copolyol | 7.00% |
| Diisopropyl Adipate | 5.00% |
| Fragrance | 0.50% |

-continued

| Phase B | | |
|---|---|---|
| Aluminum Chlorohydrate, 50% Solution | | 55.00% |
| Glycerin | | 5.00% |
| Demineralized Water | | 7.98% |
| POE (20 M) Sorbitan Monolaurate | | 0.50% |
| Polyquaternium-10 | | 0.02% |
| Refractive index: | Phase A | 1.4035 |
| | Phase B | 1.4032 |
| | Gel | 1.4033 |
| pH | | 3.76 |
| Viscosity | | 14,000 cps |
| Clarity | | 12 NTU |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A gel composition, comprising:
    a water-in-oil emulsion having a viscosity from about 7,000 cps to about 25,000 cps;
    an antiperspirant active;
    water;
    a silicone gelling agent; and
    one or more silicone oils.

2. The gel composition of claim 1, wherein the gel composition has a clarity from about 30 NTU or less.

3. The gel composition of claim 2, wherein the clarity is from about 10 NTU to about 20 NTU.

4. The gel composition of claim 1, wherein the viscosity is from about 12,000 cps to about 21,000 cps.

5. The gel composition of claim 1, wherein the antiperspirant active is present in an amount about 5 wt. % to about 50 wt. % based on the total weight of the gel composition.

6. The gel composition of claim 1, wherein the water is present in an amount about 25 wt. % to about 45 wt. % based on the total weight of the gel composition.

7. The gel composition of claim 1, wherein the silicone gelling agent is present in an amount about 0.1 wt. % or more based on the total weight of the gel composition.

8. The gel composition of claim 7, wherein the silicone gelling agent is about 0.5 wt. % to about 5 wt. % based on the total weight of the composition.

9. The gel composition of claim 1, wherein the one or more silicone oils are present in an amount about 9 wt. % or more based on the total weight of the gel composition.

10. The gel composition of claim 7, wherein said one or more silicone oils comprise one or more non-volatile silicone oils and one or more volatile silicone oils.

11. The gel composition of claim 1, wherein the composition has an index of refraction from about 1.39 or more.

12. The gel composition of claim 1, wherein the water-in-oil emulsion has an inner water phase and an outer silicone phase, and wherein the water phase and silicone phase have indices of refraction within 0.0004 of each other.

13. The gel composition of claim 1, further comprising from about 0.1 wt. % to about 2 wt. % of a formaldehyde donor.

14. The gel composition of claim 13, wherein the formaldehyde donor is selected from the group consisting of diazolidinyl urea, imidazolidinyl urea, DMDM hydantoin, Quaternium-15 and a combination thereof.

15. A method of decreasing perspiration from human skin, comprising:
    applying to the skin an antiperspirant gel composition, the composition being a water-in-oil emulsion having a viscosity from about 7,000 cps to about 25,000 cps, the composition further comprising an antiperspirant active, water, a silicone gelling agent, and one or more silicone oils.

16. The method of claim 15, wherein the composition has a clarity of about 30 NTU or less.

17. The method of claim 16, wherein the clarity is from about 10 NTU to about 20 NTU.

18. The method of claim 15, wherein the antiperspirant active is about 5 wt. % to about 50 wt. % based on the total weight of the composition.

19. The method of claim 15, wherein the water is about 25 wt. % to about 45 wt. % based on the total weight of the composition.

20. The method of claim 15, wherein the silicone gelling agent is about 0.1 wt. % or more based on the total weight of the composition.

21. The method of claim 20, wherein the silicone gelling agent is about 0.5 wt. % to about 5 wt. % based on the total weight of the composition.

22. The method of claim 15, wherein the one or more silicone oils is about 9 wt. % or more based on the total weight of the composition.

23. The method of claim 22, wherein the one or more silicone oils comprise one or more non-volatile silicone oils and one or more volatile silicone oils.

24. The method of claim 15, wherein the viscosity is from about 12,000 cps to about 21,000 cps.

25. The method of claim 15, wherein the water-in-oil emulsion has an inner water phase and an outer silicone phase, and wherein the water phase and silicone phase have indices of refraction within 0.0004 of each other.

26. The method of claim 15, wherein the composition has an index of refraction from about 1.39 or more.

27. The method of claim 15, wherein the composition is substantially transparent.

28. The method of claim 15, wherein the composition further comprises about 0.1 wt. % to about 2 wt. % of a formaldehyde donor.

29. The method of claim 28, wherein the formaldehyde donor is selected from the group consisting of diazolidinyl urea, imidazolidinyl urea, DMDM hydantoin, Quaternium-15, and a combination thereof.

30. A method of imparting quick drying antiperspirant protection to skin comprising applying to the skin the composition of claim 1.

31. A method of enhancing the effectiveness of an antiperspirant composition comprising including in the composition a formaldehyde donor.

32. The method of claim 31, wherein the formaldehyde donor is selected from the group consisting of diazolidinyl urea, imidazolidinyl urea, DMDM hydantoin, Quaternium-15, and a combination thereof.

33. A gel composition, comprising:
    a water-in-oil emulsion having a viscosity from about 7,000 cps to about 25,000 cps, the emulsion having water;
    a silicone gelling agent; and
    one or more silicone oils.

34. The gel composition of claim 33, wherein the gel composition has a clarity from about 30 NTU or less.

35. The gel composition of claim 34, wherein the clarity is from about 10 NTU to about 20 NTU.

36. The gel composition of claim 33, wherein the viscosity is from about 12,000 cps to about 21,000 cps.

37. The gel composition of claim 33, wherein the water is present in an amount about 25 wt. % to about 45 wt. % based on the total weight of the gel composition.

38. The gel composition of claim 33, wherein the silicone gelling agent is present in an amount about 0.1 wt. % or more based on the total weight of the gel composition.

39. The gel composition of claim 38, wherein the silicone gelling agent is about 0.5 wt. % to about 5 wt. % based on the total weight of the composition.

40. The gel composition of claim 33, wherein the one or more silicone oils are present in an amount about 9 wt. % or more based on the total weight of the gel composition.

41. The gel composition of claim 33, wherein said one or more silicone oils comprise one or more non-volatile silicone oils and one or more volatile silicone oils.

42. The gel composition of claim 33, wherein the composition has an index of refraction from about 1.39 or more.

43. The gel composition of claim 33, wherein the water-in-oil emulsion has an inner water phase and an outer silicone phase, and wherein the water phase and silicone phase have indices of refraction within 0.0004 of each other.

44. The gel composition of claim 33, further comprising an antiperspirant active.

45. The gel composition of claim 33, further comprising about 0.1 wt % to about 2 wt % of a formaldehyde donor.

46. The gel composition of claim 33, wherein the formaldehyde donor is selected from the group consisting of diazolidinyl urea, imidazolidinyl urea, DMDM hydantoin, Quaternium-15 and a combination thereof.

47. The gel composition of claim 33, wherein the viscosity is about 18,000 cps to about 21,000 cps.

48. The gel composition of claim 34, wherein the clarity is about 5 NTU to about 30 NTU.

49. The gel composition of claim 36, wherein the viscosity is about 18,000 cps to about 21,000 cps.

50. The gel composition of claim 42, wherein the index of refraction is less than about 1.41.

51. The gel composition of claim 42, wherein the index of refraction is about 1.39 to about 1.41.

52. The gel composition of claim 44, wherein the antiperspirant active is present in an amount about 5 wt% to about 50 wt% based upon the total weight of the gel composition.

53. The gel composition of claim 44, wherein the antiperspirant active is present in an amount about 15 wt% to about 25 wt% based upon the total weight of the gel composition.

* * * * *